United States Patent [19]

Callan et al.

[11] Patent Number: 5,256,376

[45] Date of Patent: Oct. 26, 1993

[54] AGGLUTINATION DETECTION APPARATUS

[75] Inventors: Gerald W. Callan, Brewster; William D. Corry, Larchmont; Richard E. Scordato, Mount Kisco; John G. Gorman, New York, all of N.Y.

[73] Assignee: Medical Laboratory Automation, Inc., Pleasantville, N.Y.

[21] Appl. No.: 758,772

[22] Filed: Sep. 12, 1991

[51] Int. Cl.$^5$ .................... G02N 21/05; G01N 21/07
[52] U.S. Cl. ...................................... 422/102; 422/72; 422/73; 422/81; 422/103; 422/104; 436/809; 435/287; 356/246; 356/440
[58] Field of Search .................... 422/72, 73, 81, 82, 422/82.05, 99, 100, 102, 103, 104; 436/809; 356/246, 427, 440; 435/287

[56] References Cited

U.S. PATENT DOCUMENTS

| | | | |
|---|---|---|---|
| 3,763,374 | 10/1973 | Tiffany et al. | 250/363 |
| 3,864,089 | 2/1975 | Tiffany et al. | 23/258.5 |
| 3,890,101 | 6/1975 | Tiffany et al. | 23/259 |
| 4,148,607 | 4/1979 | Bernoco et al. | 23/230 B |
| 4,350,283 | 9/1982 | Leonian | 233/26 |
| 4,431,606 | 2/1984 | Revillet et al. | 422/102 |
| 4,456,581 | 6/1984 | Edelmann et al. | 422/72 |
| 4,469,793 | 9/1984 | Guigan | 436/45 |
| 4,557,600 | 12/1985 | Klose et al. | 356/246 |
| 4,566,790 | 1/1986 | Mandle | 356/246 |
| 4,580,897 | 4/1986 | Nelson et al. | 356/246 |
| 4,597,944 | 7/1986 | Cottingham | 422/73 |
| 4,683,120 | 7/1987 | Meserol et al. | 422/72 |

Primary Examiner—James C. Housel
Assistant Examiner—David Redding
Attorney, Agent, or Firm—Wolf, Greenfield & Sacks

[57] ABSTRACT

A method and apparatus are provided for use with a centrifuge to analyze reactants. The apparatus includes at least one cuvette having at least one chamber. The chamber has a radially outward wall which provides a base upon which reactants can be pelleted when the device is rotated about a centrifugal axis. Each cuvette includes one or more openings for introducing fluids to the cuvette and includes a channel positioned adjacent to the radially outward wall for removing fluids from the chamber. Pressure is applied to the chamber to force fluids therefrom, through the channel. A hold down device is also provided through which fluid and/or pressure may be passed with respect to the cuvette. The invention also provides a method for determining the existence and degree of agglutination of reactants in a first fluid suspension and contained in a single reaction vessel using a photodetector.

34 Claims, 11 Drawing Sheets

AGGLUTINATION DETECTION APPARATUS

BACKGROUND OF THE INVENTION

This invention relates to agglutination detection and more particularly to a method and apparatus to continuously perform a centrifugal agglutination and detection operation.

Agglutination is the clumping of a suspension of cellular or particulate antigen by a reagent, usually an antibody. Agglutination can occur when an antibody binds to corresponding antigen sites on at least two cells or particles. Large clumps of agglutinated particles, observable by the naked eye, can be formed if the strength of the bonds formed by the antibodies between particles is sufficient to withstand the shear forces tending to break up the agglutinates. Smaller clumps still may be observable with the aid of a microscope or by photodetection means.

The widespread us of agglutination based tests has led to many attempts to automate the procedure. One attempt used in blood banking employs a U-bottomed microplate that allows the simultaneous testing of many individual samples. Typically, erythrocytes are mixed with anti-sera or a plasma sample which might aggregate them. After an appropriate incubation period, the erythrocytes are centrifuged in the microplate and then are resuspended manually or with mechanized agitation. The erythrocytes are allowed to settle and the pattern of cells formed after settling is examined. If the cells are agglutinated, a clump of erythrocytes or "cell button" will settle to the bottom of the U shaped well. Unagglutinated cells will be more uniformly dispersed over the bottom of the well after similar treatment. Differentiation between aggregated and unaggregated erythrocytes can be automated with a photometric detection system that discriminates between the pattern formed by a cell button and that formed by uniformly settled cells.

The foregoing technique has many drawbacks. For example, some agglutination reactions of interest are held together by weak bonds and the agitation may break up the weak agglutination. Thus, there is limited ability to discriminate between no agglutination and weak agglutination. Furthermore, standardizing shear stresses exerted upon the cells during agitation is difficult as these stresses are affected by sample dependent properties which the experimenter cannot control.

Alternative approaches are described in U.S. Pat. No. 4,303,616 and 4,466,740. A microtiter plate having wells with protrusions or depressions on an inclined bottom surface is used to eliminate resuspension and centrifugation steps. As before, erythrocytes and plasma or anti sera are mixed in wells and, after an appropriate incubation period, the reactants simply are allowed to settle onto the inclined bottom surface of the microplate. Essentially, the cells initially captured by the protrusions or depressions act as a base upon which agglutination occurs. When agglutination is present, a greater percentage of cells are captured by the protrusions or depressions, and many fewer cells settle to the bottom of the test vessel. The difference in the pattern produced when there is agglutination as opposed to when there is no agglutination can be read with a photometric detection system.

The failure of the foregoing system to use centrifugal force to pack the erythrocytes has several drawbacks. First, the cells take a long time to settle, thus making this system impractical for many applications. Second, the system lacks the sensitivity achieved when cells are packed together with centrifugal force. Third, the settling patterns created under such a system are extremely delicate and subject to disruption by slight motion. Therefore, in one commercial embodiment of the foregoing system, high cost vibration free transport mechanisms are required for the microplates. Fourth, only positive or negative results are provided and, thus, it is not possible to grade the strength of the agglutination reaction. Finally, the foregoing system does not integrate well with protocols that require washing the cells.

U.S. Pat. No. 4,148,607 discloses an agglutination test that utilizes a vessel having a sloped rear wall upon which reactants are pelleted by centrifugation. After cessation of centrifugation, there is a waiting period during which the fluid the cells were pelleted in is allowed to fall away from the "cell button". The "cell button" is then given the opportunity to move under the influence of gravity along the sloped rear wall. The movement is detected by an optical instrument and correlated to the presence or absence of agglutination.

Since agglutination occurs under the forces of centrifugation, this method does not have all of the same drawbacks as U.S. Pat. Nos. 4,303,616 and 4,466,740. However, the sensitivity and reproducibility of the method is dependent upon the environment which the agglutinated particles, e.g., red blood cells, experience during the settling process. In the previous technique, the flow of the fluid along the sloped wall is dependent on the fluid wall interface and the design of the apparatus allowed fluid to flow away from the aggregated red blood cells, thereby exposing the cells to air during settling and causing the buoyant density of the cells to fluctuate several fold. As a consequence, the sensitivity and reproducibility of the prior method also varied.

SUMMARY OF THE INVENTION

It is therefore an object of the invention to provide an agglutination detection method and apparatus with improved system throughput.

A more specific object of the invention is to provide such a method and apparatus that can rapidly detect agglutination.

Another object of the invention is to provide an agglutination detection method and apparatus which utilize centrifugal force to enhance the agglutination reaction and to allow the detection of weak agglutination.

Another object of the invention is to provide an agglutination detection method and apparatus capable of grading the strength of an agglutination reaction.

Another object of the invention is to provide an agglutination device which will increase the sensitivity and reproducibility with which aggregated red blood cells are detected by controlling the medium through which the aggregated red blood cells are allowed to settle.

Another object of the invention is to provide an agglutination device characterized in having a relatively reproducible distance through which agglutinated products are centrifuged, which distance does not vary appreciably as a function of fluid volume.

Another object of the invention is to provide an agglutination detection method and apparatus wherein a multiplicity of agglutination reactions can be monitored by a single photometric detection system during centrifugation.

Yet another object of the invention is to provide a hold down device for maintaining an agglutination apparatus containing a plurality of cuvettes in proper position during centrifugation.

Still another object of the invention is to provide an agglutination detection method and apparatus that allow for simple and efficient washing of reactants during and after centrifugation in a single reaction vessel.

Another object of the invention is to provide a agglutination detection apparatus having a fluid removal channel to allow for continuous centrifugation and washing of reactants within a single vessel. More specifically, the invention should provide for the removal of all but a very small and reproducible amount of fluid from the agglutination detection apparatus chamber in response to the application of differential pressure thereto, without removing particulate reactants during centrifugation.

These and other objects are achieved by providing an apparatus for analyzing reactants and adapted for use with a device which will rotate the apparatus about a centrifugal axis. The apparatus includes at least one cuvette having at least one chamber with a radially outward wall. The wall provides a base upon which reactants can be pelleted when the apparatus is rotated about a centrifugal axis. The cuvette includes means for introducing fluids or a fluid suspension into the chamber and a channel positioned adjacent to the radially outward wall for removing fluids or a fluid suspension from the chamber. As defined herein, the terms fluid or fluids include fluids having reactants suspended therein (i.e., a fluid suspension). Additionally, the apparatus includes means for applying differential pressure to the cuvette to force fluid or a fluid suspension from the chamber through the channel. In preferred embodiments, the apparatus includes a plurality of cuvettes and is adapted for use with a centrifuge rotor.

The apparatus of the present invention can be used to analyze reactants which are components of an agglutination reaction. In this application, the cuvette includes optical windows in the chamber for allowing photodetection of the agglutination reaction. In order to effect the removal of substantially all the supernatant from the cuvette chamber without removing particulate reactants during centrifugation, the apparatus can include means which apply positive air pressure or, in the alternative, means which apply vacuum pressure.

In one embodiment, the apparatus includes a cuvette having a plurality of chambers, each chamber having means for preventing fluid flow between chambers in the absence of a centrifugal force. For example, the cuvette can have a first chamber located radially inward of a second chamber, and a third chamber located radially outward of the second chamber. In such an arrangement, the chambers are in fluid communication and the first and second chambers include first and second ports for introducing fluids or a fluid suspension. The third chamber includes a radially outward wall which provides a base upon which reactants are pelleted when the apparatus is rotated about a centrifugal axis. The cuvette also includes a channel positioned adjacent to the radially outward wall in communication with the third chamber for removing fluids or a fluid suspension. Preferably, the channel forms an obtuse angle with the third chamber and the third chamber includes a generally L-shaped side wall having an obtuse angle. A central port communicates with the first, second and third chambers.

The apparatus of this embodiment may also include a fourth chamber for preventing a syphoning effect from forming in the channel joining the third and fourth chambers. Preferably, the fourth chamber is in fluid communication with at least one radially outward retaining chamber for collecting fluid forced from the third chamber. The apparatus may further include a fifth chamber for adding additional reagents. The fifth chamber is located radially inward from the third chamber, adjacent to the second chamber, and in fluid communication with the third chamber. The fifth chamber includes an access port for introducing additional reagent thereto and means for preventing fluid flow between the fifth and third chambers in the absence of centrifugal force. The apparatus of this embodiment may also include a sixth chamber in communication with the fluid retaining chamber. The sixth chamber contains air vent holes for venting air pressure applied to the apparatus during its operation.

In another embodiment, the apparatus includes at least one cuvette having a channel communicating at one end with a rear portion of the cuvette chamber and at an opposite end with a radially inward exit pipe. The exit pipe has a small diameter such that surface tension will stop capillary flow at an exit of the exit pipe. In this embodiment, the chamber comprises first and second portions, with the first portion located radially inward of the second portion and including a port for introducing fluid or a fluid suspension. The second portion includes the channel located generally sufficiently close to the radially outward wall to effectively remove fluids or a fluid suspension from the second portion of the chamber, without removing particulate reactants during centrifugation.

The present invention also provides a hold-down device for use with an agglutination cuvette when the cuvette is positioned on a device which will rotate it about a centrifugal axis. The hold down device maintains a cuvette or a plurality of cuvettes arranged as a disk in proper position on a centrifuge rotor during centrifugation. Specifically for one embodiment, the hold down device includes a portion which effects the removal of fluids or a fluid suspension from the cuvette, the hold down device having a housing which encloses a series of fluid withdrawal channels through which fluids or a fluid suspension can be withdrawn from the cuvette during centrifugation. Alternatively, the housing encloses a fluid dispensing tube located co axially with an air pipe through which fluid or air can be introduced to a cuvette or plurality of cuvettes during centrifugation. The hold-down device includes sealing mean to attach the device to the cuvette or for sealing at least one part of a plurality of cuvettes.

Furthermore, the invention provides for photometrically determining the existence and degree of agglutination of reactants. The photometric detection system includes a light source emitting a light beam, an optical window through which light can communicate with the chamber of the cuvette, and a light beam detector. In operation, the reactants, including particulate reactants, are introduced into a chamber within a cuvette and allowed to react in the chamber. The cuvette may optionally be incubated to enhance the agglutination reaction before applying differential pressure and centrifugal force to the cuvette to remove the first fluid from the chamber. A second fluid is introduced into the chamber and the cuvette is subjected to a repetitive forward and reverse rotation about the centrifugal axis to resuspend the particulate reactants. As the cuvette is centrifuged, a first optical density profile is obtained by photodetecting a reduction in optical density to a minimum value as the particulate reactants are pelleted. A second optical density profile is obtained by photodetecting an increase in optical density as the pelleted particulate reactants are allowed to settle under gravity. The existence and degree of the agglutination reaction is assessed by comparing the optical density profiles obtained for different reactants. For example in regard to the first optical density profile, the starting optical density (i.e., the optical density at time zero) is indicative of the strength of the reaction. The lower the starting optical density, the stronger the agglutination reaction. Conversely, a high starting optical density is indicative of a negative agglutination reaction.

Accordingly, the invention further provides an apparatus characterized in having a reproducible pelleting distance through which particulate reactants are centrifuged. The shapes of the pelleting curves in the above described optical density profiles are thereby stabilized, thus facilitating interpretation of the pelleting curves and gradation of agglutination reaction strength.

The foregoing and other objects, features and advantages of the invention will be apparent from the following more particular descriptions of preferred embodiments of the invention as illustrated in the accompanying drawings.

DETAILED DESCRIPTION

Figure 1:
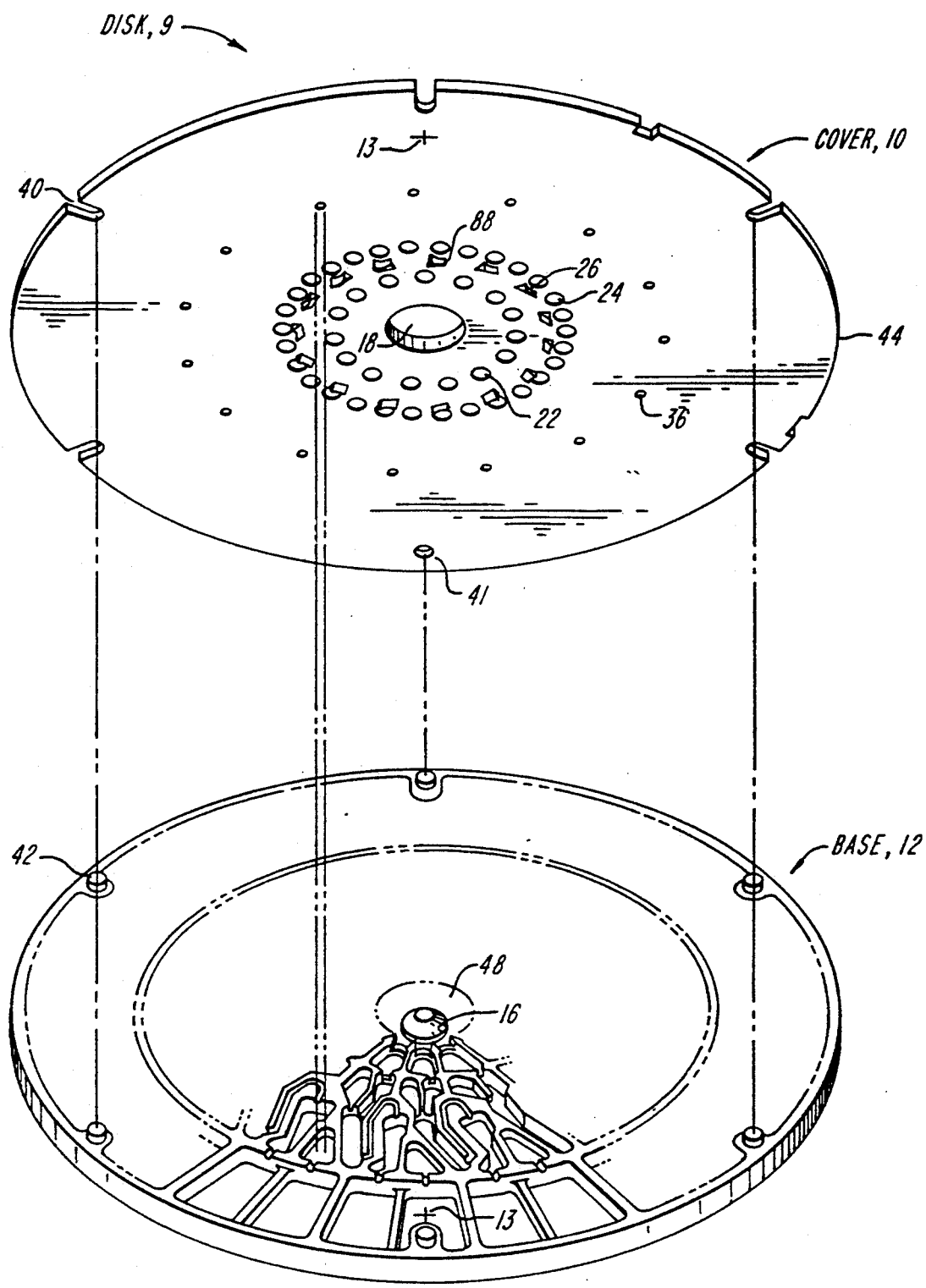
FIG. 1 is an exploded, front view of a base and cover in accordance with a first embodiment of the invention.
Figure 2:
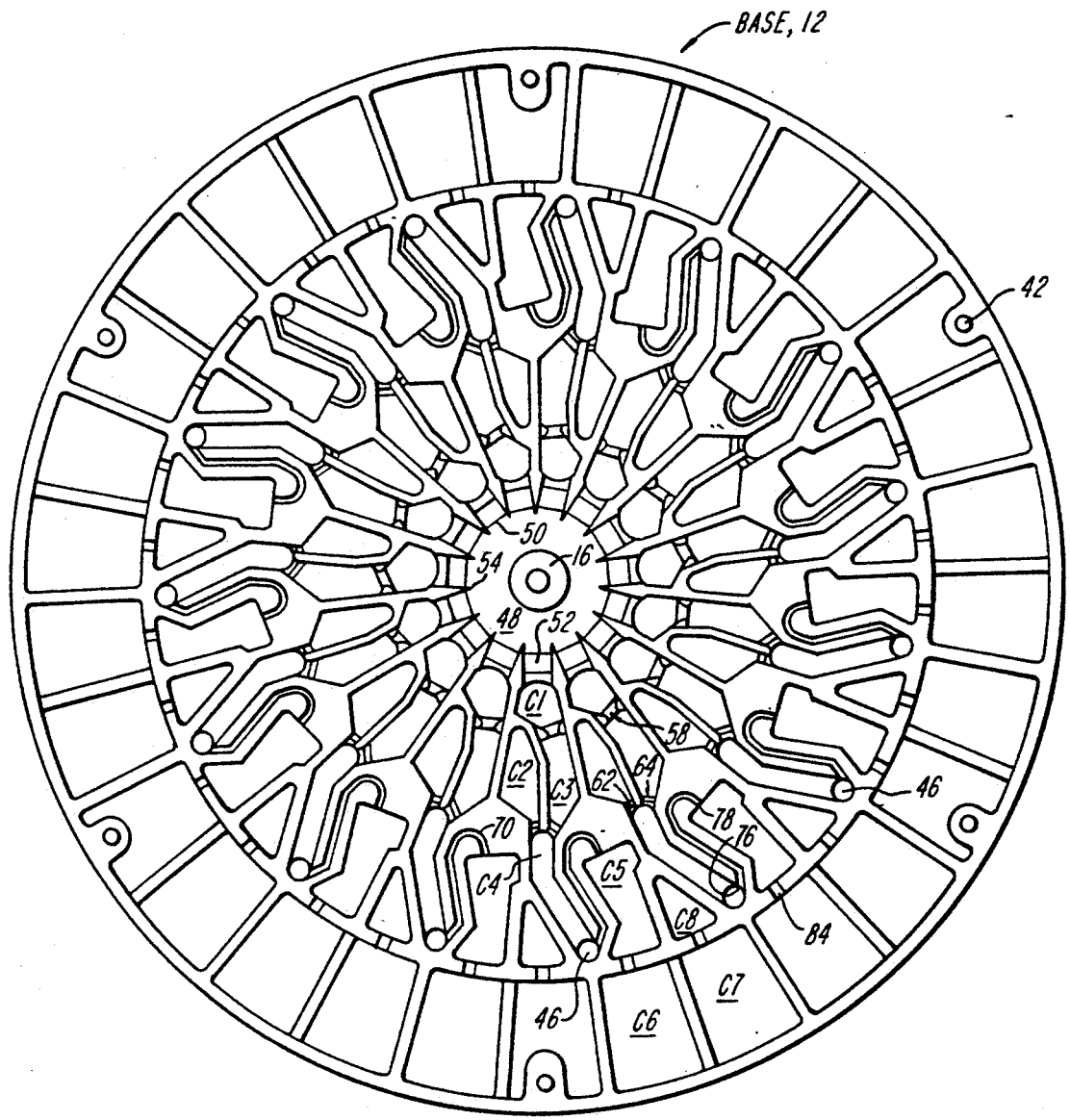
FIG. 2 is an enlarged, top view of the base shown in FIG. 1.
Figure 3:
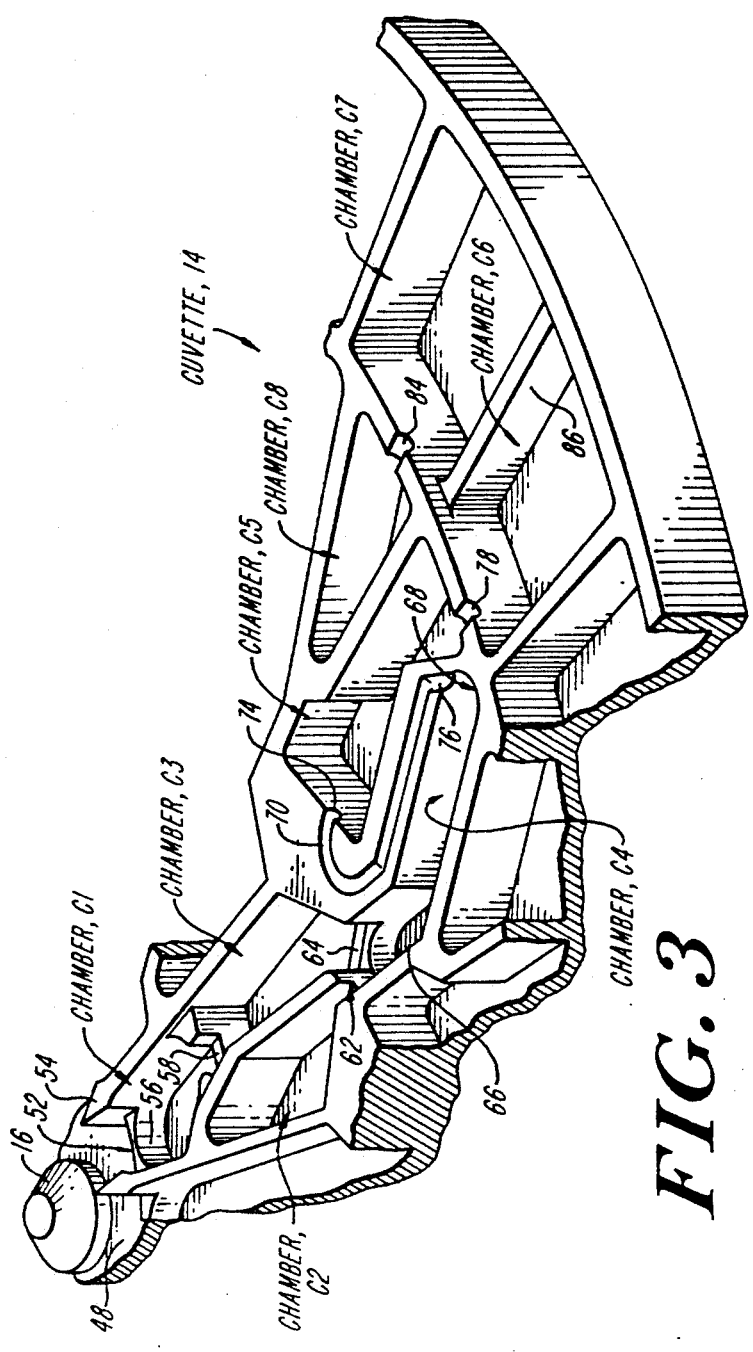
FIG. 3 is an enlarged, perspective view of one test unit or cuvette of the base shown in FIG. 1.

Referring to FIGS. 1-5, one embodiment of the invention is a unitary multichambered, disposable disk 9, formed of a cover 10 and a base 12. The disk 9 is divided by appropriate walls into fifteen identical agglutination cuvettes 14, the base for a single one of which is shown in FIG. 3. Each cuvette is spaced radially with respect to a central rotor positioning inverted well 16 and is defined by a series of barrier walls forming a series of interconnected chambers. For the purpose of illustration, the invention will be described with reference to base structure 12. However, it should be understood that the words "cuvette" and "chamber" when applied to the base are intended to mean the cuvettes or chamber formed when base 12 and cover 10 are assembled and attached.

Focusing on base structure 12 as illustrated in FIGS. 1, 2 and 3, the walls separating the cuvettes and chambers of each cuvette are generally of uniform height and form the surface upon which cover 10 rests. Some of the walls are barrier walls in that they restrict fluid communication between the chambers formed on either side of the walls. Other walls of an individual chamber may be interrupted by a variety of openings having different configurations, which together with the spacings and shapes of the chambers, provide for the controlled movement of fluids and fluid suspensions through the chambers of cuvette 14 during the agglutination reaction.

The rotor positioning inverted well 16, located in the center of a central channel 48, serves as a point of contact with a centrifuge (not shown). Central channel 48 is defined by a central channel wall 50 which has a multiplicity of ramps 52 and tapered spokes 54 pointing inward toward the center of rotation (i.e. toward rotor positioning well 16). Spokes 54 represent the terminal extensions of each cuvette wall. Ramps 52 promote unidirectional fluid communication from central channel 48 to a "C1" chamber of each cuvette 14 by acting as a barrier between the central channel and the "C1" chamber when disk 9 is not rotating. When the disk is subjected to a centrifugal force, fluid is injected in a stream aimed radially outwardly into the central channel 48, where it is driven up each ramp 52 and into each corresponding "C1" chamber.

Figure 4:
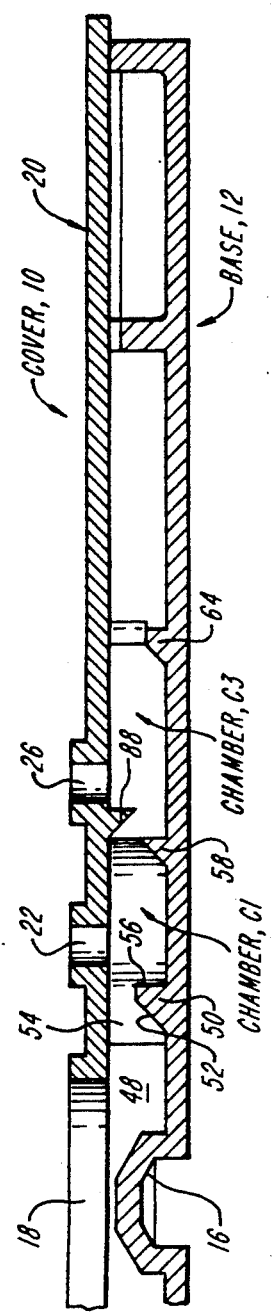
FIG. 4 is a partial cross sectional view of the cover and base shown in FIG. 1 when assembled.

In order to more simply describe the invention, a single cuvette 14 (without attached cover) is illustrated in FIG. 3. It will be understood, however, that the cuvettes are identical and that the discussion in connection with FIG. 3 applies to each of the radially aligned cuvettes 14 of disk 9. Cuvette 14 is comprised of a system of eight chambers in fluid communication by a series of passageways of various sizes and shapes. Fluid enters cuvette 14 at chamber "C1" either by way of central channel 48 or via a "C1" access port 22 located in cover 10 (FIGS. 1 and 4). The size of the "C1" chamber is selected to be able to contain the volume of reagent required for the agglutination reactions.

The "C1" chamber is generally pentagonal in shape and is formed of three side walls, a curvilinear face 56 forming part of wall 50, and a ramp 58 in the side wall leading into a "C3" chamber. The three side walls of the "C1" chamber extend from the base to the cover and are barrier walls. Ramp 52 extends upwardly from the bottom of central channel 48 to the flat top surface of wall 50. Curvilinear face 56 extends to the other side of the top flat surface. Ramp 52 is of sufficient height above the floor of central channel 48 to prevent fluid flow from the central channel into the "C1" chamber in the absence of a centrifugal force. Likewise, ramp 58 extends upwardly from the floor of the "C1" chamber to a height sufficient to serve as a barrier between the "C1" and "C3" chambers and to prevent the premature mixing of reagents and samples prior to the application of a centrifugal force. The portions of the walls on either side of ramp 58 funnel in toward ramp 58 to ensure that upon application of a centrifugal force, all of the material exiting the "C1" chamber is channelled into the "C3" chamber. Base 12 of disk 9 contains several ramp structures in addition to ramps 52 and 58. In a preferred embodiment, the pitch of the ramp structures ranges from approximately 30° to 60°. In a most preferred embodiment, the pitch of the ramp structures is approximately 60°.

A "C2" chamber is located generally radially outwardly of the "C1" chamber and shares a portion of one side wall with the "C1" chamber. The "C2" chamber is generally pentagonal in shape with four of its five walls extending from the floor of the chamber to cover 10, effectively sealing the "C2" chamber from fluid communication with all chambers except for a "C4" reaction chamber (described below). Fluid can be introduced into the "C2" chamber via a "C2" access port 24 (FIG. 1). Fluid can exit the "C2" chamber via a ramp 62 which extends upwardly from the floor of the "C2" chamber toward the "C4" reaction chamber and forms an opening between the two chambers. In one embodiment, ramp 62 has the steepest pitch and greatest height of all of the base structure ramps.

A "C3" chamber is located adjacent to and shares two side walls with the "C2" chamber and one side wall with the "C1" chamber. The "C3" chamber is generally hexagonal in shape with four of six walls extending from the floor of the chamber to the cover 10. The remaining two side walls each include ramp structures. Fluid may be introduced into the "C3" chamber via a "C3" access port 26 (FIGS. 1 and 4) in cover 10. Alternatively, fluid may enter the "C3" chamber via ramp 58 (FIGS. 3 and 4).

Fluid exits the "C3" chamber via a ramp 64 which extends upwardly from the floor of the "C3" chamber toward the "C4" reaction chamber and forms an opening between the two chambers. Ramp 64 is located substantially opposite ramp 58 and is of sufficient height to serve as a barrier between the "C3" and "C4" chambers in the absence of a centrifugal force. Like ramp 58, portions of the barrier walls of the "C3" chamber on either side of ramp 64 funnel in toward the ramp to ensure that upon application of a centrifugal force, all of the material exiting the "C3" chamber is channelled into the "C4" reaction chamber. A second ramp 62, is formed on the wall separating the "C2" and "C4" chambers and also provides for the introduction of reagents into the "C4" chamber.

Figure 5:
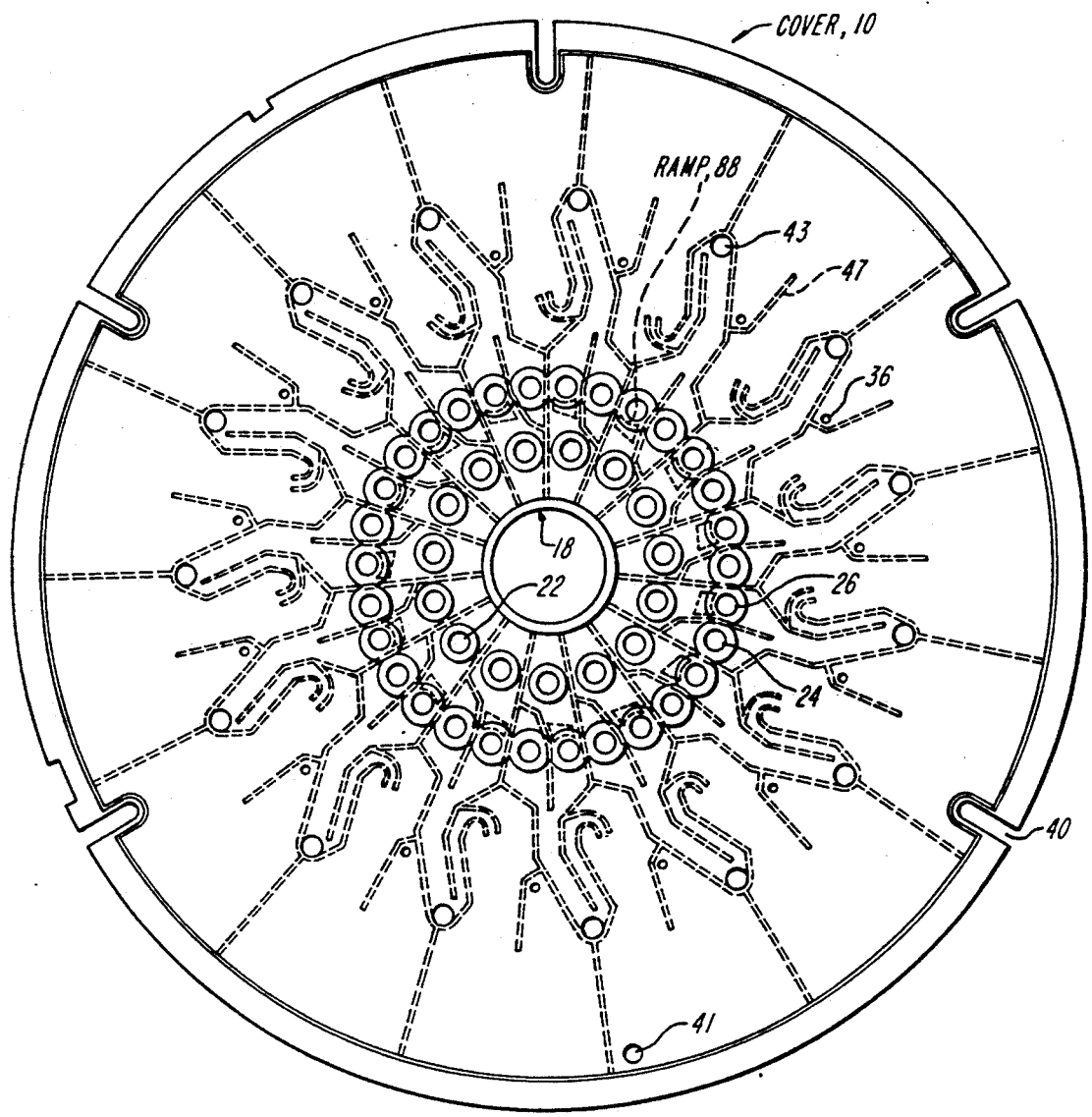
FIG. 5 is a top view of the cover for the embodiment shown in FIG. 1.

The "C4" reaction chamber is formed of barrier walls in the shape of an oblongated L. The principle structural features of the "C4" chamber are a bend 66, a rear wall 68 and optical windows 43 and 46 (FIGS. 2 and 5). Bend 66 preferably is at an angle of approximately 150°. Rear wall 68 is substantially vertical and extends from the floor of base 12 to cover 10. Rear wall 68 is preferably curvilinear, but is not limited to a curvilinear shape, and may for example, be V shaped. Optical window 46 is located in the floor of the base adjacent to rear wall 68 of the "C4" chamber (FIG. 2). The cover contains a corresponding optical window 43 (FIG. 5), positioned such that optical windows 43 and 46 are aligned when cover 10 and base 12 are attached. Each optical window is recessed, optically clear and has an optical surface finish.

Figure 14:
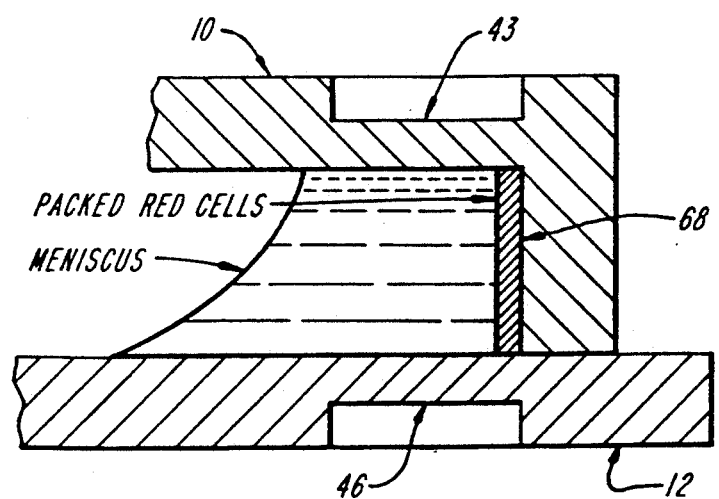
FIG. 14 is a side cross sectional view of a reaction chamber of the cuvette of FIG. 3 shown with packed cells immersed in fluid.

The overall size and shape of the "C4" reaction chamber is narrow enough to facilitate the capillary retention of a non wetting fluid in the "C4" chamber. Although the agglutination device is preferably made of a material (e.g., polystyrene) which is not wetted by water, the presence of protein in the reactants does result in wetting to some degree. Accordingly, cells centrifugally packed against rear wall 68 of the "C4" chamber are continually immersed in fluid, as is shown in FIG. 14. Thus, the descent of cells into the field of vision defined by optical windows 43, 46 is solely determined by gravity and is unaffected by the dynamics of an air-fluid interface.

A channel 70, one end of which is positioned adjacent to rear wall 68 of the "C4" chamber serves as a conduit for fluid from the "C4" chamber to the "C5" chamber (FIG. 3). The channel is formed in the barrier wall that separates these two chambers. A channel entry hole 76 is located above the floor of the "C4" chamber in the side wall separating the "C4" and "C5" chambers. The positioning of channel entry hole 76 above the floor of the "C5" chamber helps prevent the backflow of waste materials into the "C4" reaction chamber. Further, the positioning of channel 70 radially inwardly of rear wall 68 of the "C4" chamber ensures that cells which have inadvertently entered channel 70, will be directed back into the "C4" reaction chamber when disk 9 is subjected to a centrifugal force. The exact positioning of channel entry hole 76 relative to rear wall 68 of the "C4" chamber is important in balancing the need to optimally remove waste fluids against the desire to minimally disturb the agglutinated cells and to maintain a relatively constant cell number and residual volume. With entry hole 76 near, but not at rear wall 68, this objective can generally be achieved for given reactants at a selected centrifugation rate. The positioning of the channel opening thus permits the reproducible washing and packing of cells against the rear wall of the reaction chamber. The design of the invention obviates the problem of variable settling rates as a function of variable cell number by ensuring that cells are not removed from the reaction chamber when fluid is decanted from the chamber.

A "C5" chamber is formed of seven side walls extending from the floor of the base 12 to the cover 10. The "C5" chamber functions to break the syphoning effect created by channel 70. Channel 70 includes a channel exit hole 74 at the opposite end of channel entry hole 76 and located at the top of a radially inward "C5" side wall. The application of air pressure to cuvettes 14 of disk 9 via central port 18 forces waste fluids to flow into the "C5" chamber. Once fluid has entered the "C5" chamber, it is expelled from the chamber via hole 78 in the side wall of the "C5" chamber. The application of centrifugal force and/or positive air pressure, forces waste fluid from the "C5" chamber through hole 78 and into the "C6" chamber.

The "C6" chamber is located adjacent to and shares one side wall with the "C5" chamber. Three of the four walls of the "C6" chamber extend from the floor of the chamber to cover 10. A fourth wall 86, shared with a "C7" chamber, provides structural support but permits fluid communication between the "C6" and "C7" chambers.

Both the "C6" and "C7" chambers are formed in the shape of a trapezoid having three barrier walls and one shared non-barrier wall. The only structural features present in some of the "C6" chambers which are absent in the "C7" chamber are orientation pins 42, slots 40 or a hole 41 (FIG. 1). Since the volume defined by the "C6" and "C7" chambers is more than adequate to contain the amount of waste fluid generated, the inclusion of these orientation structures in the "C6" chambers does not impose any limitations on the invention.

A hole 84 providing fluid communication between the "C7" chamber and a "C8" chamber is located in the top of a radially inward "C7" barrier wall. Application of a centrifugal force forces fluid away from hole 84 resulting in fluid remaining in the "C7" chamber.

The "C8" chamber is formed of three barrier walls. Air vent holes 36, located in cover 10 above each "C8" chamber, prevent the creation of an air lock when air pressure is applied to a plurality cuvettes in disk 9 (FIG. 1). The positioning of air vent hole 36 closest to the center of rotation (and coincidentally furthest from hole 84) in conjunction with the positioning of the "C7" and "C8" chambers so that centrifugal force prevents fluid from entering the "C8" chamber, substantially reducing the formation of potentially hazardous aerosols from the waste fluid contained in the "C7" chamber when air pressure is applied to remove waste fluid from the "C4" reaction chamber.

FIG. 5 illustrates the top of a transparent cover 10 of the invention. Proceeding radially outwardly, central port 18 serves as a common entry point for the introduction of wash solutions or air into each cuvette 14. Central port 18 is surrounded by an arrangement of fifteen evenly spaced and radially positioned "C1" chamber access ports 22, an arrangement of thirty smaller access ports 24, 26 and a further arrangement of fifteen air vent holes 36. The bottom side of the cover contains raised ridges 47 and ramps 88 (viewed through the top side of a cover as shown in FIG. 5). Ramps 88, located above the juncture of the "C1" and "C3" chambers (FIG. 4), function to reduce cross contamination between these two chambers.

Cover 10 and base 12 must be carefully aligned when assembled to ensure a properly functioning cuvette. The correct orientation of the cover relative to the base is accomplished by five orientation slots 40 and one orientation hole 41 located in the cover and six orientation pins 42 located in the base (FIG. 1). The unequal spacing of the orientation slots 40 and hole 41 along the periphery of cover 10 ensures a single, correct orientation between the cover and base when the orientation slots/hole and pins mate. To further facilitate orientation, both cover 10 and base 12 are etched with a single plus (+) sign 13 (FIG. 1) or other markings which must be positioned on top of one another in order for the attachment slots 40, hole 41 and pins 42 to mate. The proper orientation of base 12 and cover 10 results in the positioning of cover optical window 43 precisely above the corresponding base optical window 46. Proper orientation also results in the positioning of raised ridges 47 (FIG. 5) of the cover precisely above the barrier walls of the base. Once oriented, cover 10 and base 12 are pressed together and, for the preferred embodiment, ultrasonically welded. Ultrasonic welding results in the melting of raised ridges 47 of cover 10 against the top surface of the barrier walls, thereby forming a seal and limiting fluid communication between the chambers to the series of openings and ramps described herein.

Figure 6:
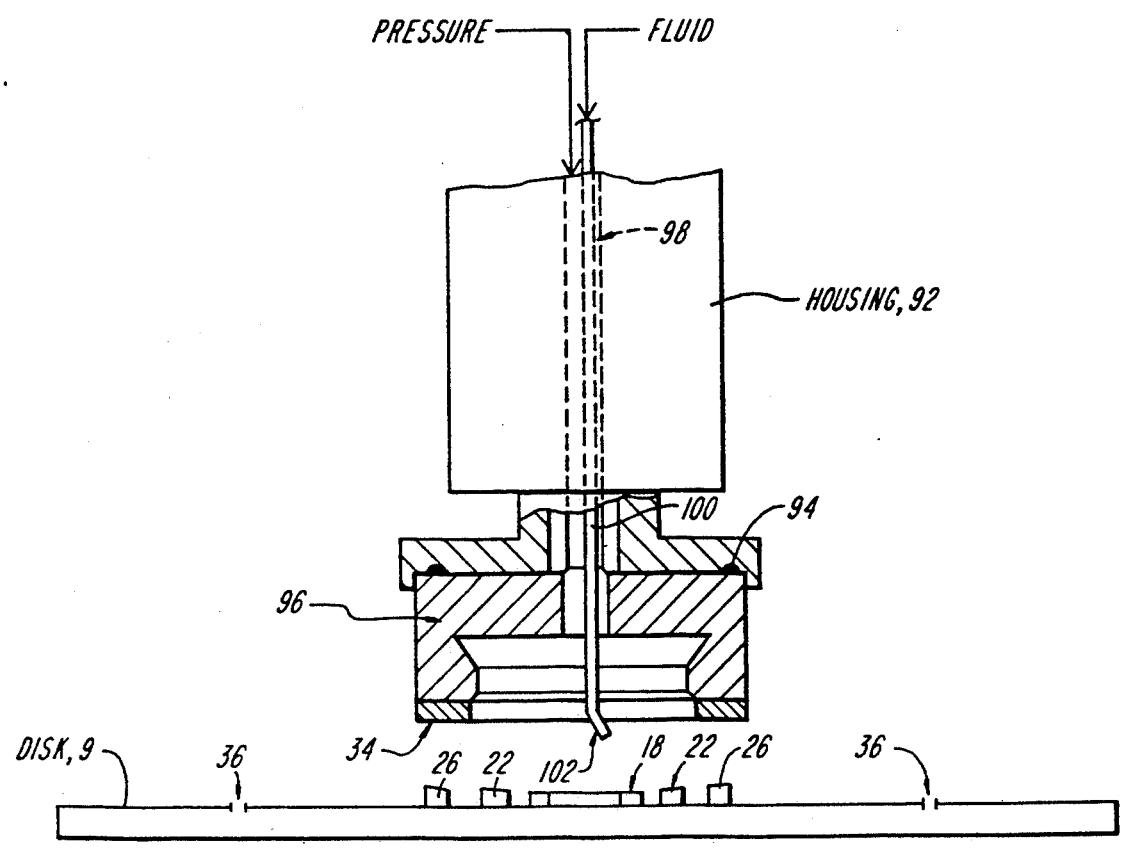
FIG. 6 is a side view, partially in cross-section of a portion of a centrifugation apparatus utilizing the embodiment of FIG. 1.

According to one preferred method of operation, disk 9 is positioned on a centrifugation apparatus (not shown) consisting in part of conventional centrifugation hardware supplemented with novel hardware to provide fluid access to central channel 48 of the disk. Referring to FIG. 6, the novel hardware consists of a fluid communication housing 92 mounted on ball bearings 94. Bearings 94 function to isolate the motion of a disk hold down 96 on which housing 92 rests and allow the housing to remain stationary when the disk hold-down is rotating in concert with a rotating disk 9. Although housing 92 does not rotate, it is constructed and arranged to move vertically, thereby facilitating placement of the disk within a centrifugation apparatus (not shown) prior to centrifugation.

A gasket 34 is glued or otherwise secured to the bottom surface of disk hold down 96. The gasket 34 is formed of urethane or a closed cell material and is dimensioned to seal chamber access ports 22, 24, 26 without obstructing central port 18 or air vent holes 36. To introduce positive air pressure into each cuvette 14, the gasket is positioned against the top surface of cover 10. The edges of ports 18, 22, 24 and 26 protrude above the top surface of the cover and provide a discrete surface area upon which gasket 34 may be placed. The protruding edges are internally tapered, with a narrower area at the top of the edge, so that drops are pulled into the disk upon centrifugation. In addition, the protruding edges effectively increase the pressure of the hold-down on the gasket by providing a smaller area of contact with the gasket. Thus, air may be introduced into a cuvette 14 via central port 18 and may exit the cuvette only via air vent hole 36.

Housing 92 includes a center shaft 98 for the introduction of air to central channel 48 of disk 9 and a co axial tube 100 for the introduction of fluid. Wash solutions such as saline are added to the disk via the co axial tube. Accordingly, co-axial tube 100 is constructed of a noncorrosive material (e.g. stainless steel). Both center shaft 98 and co axial tube 100 extend beyond the bottom surface of the housing and through the center of disk hold-down 96. When disk hold-down 96 is positioned with gasket 34 against the disk, a bottom extension 102 of co-axial tube 100 is positioned directly above central channel 48 of the disk. Fluid (e.g., saline) is added to the central channel of the disk via co axial tube 100. Air is introduced into central channel 48 via center shaft 98. The novel construction of housing 92 thus allows for the addition of fluid or air to cuvettes 14 of the disk 9 while the disk is rotating.

The agglutination device of the present invention can be used to detect the presence of either antigens or antibodies and can be disposable after use. The presence of an antibody in a test solution can be detected by mixing particles carrying the antigen with the test solution and determining whether agglutination has occurred. Conversely, the presence of an antigen on a cell in a test solution can be detected by adding an antibody of known specificity to a suspension of cells and determining whether agglutination has occurred. For example, the invention may be used to determine blood type in a forward blood typing reaction by mixing an individual's erythrocytes with antibodies directed against the various blood groups. The invention may also be used in screening assays to determine the presence or absence of a particular antibody in an individual's plasma or serum. The presence of agglutination indicates that the antibody tested for is present. Such screening assays are useful, for example, in determining the compatibility of a donor's red blood cells with a recipient. The agglutination device can be used to simultaneously perform a panel of different tests on a sample taken from a single patient. Alternatively, the device can be used to perform the same screening test for a variety of samples taken from different patients, or any combination thereof.

In order to perform a forward blood typing agglutination reaction, disk 9 is positioned in the centrifugation apparatus (not shown) and a known antisera (e.g., anti-A reagent antibody) is added to the "C1" chamber via port 22 and sample red blood cells (erythrocytes) are added to the "C3" chamber via port 26. Disk 9 is centrifuged at a speed of approximately 500 rpm to move fluids from the "C1" and "C3" chambers into the "C4" reaction chamber where reagent and sample solutions are mixed using a repetitive forward and reverse rotor rotation action. The angle 66 in the wall of the "C4" chamber facilitates agitation and mixing of the solutions as they first enter this chamber as a result of centrifugation. Disk 9 is then centrifuged at approximately 4000 rpm to pack the cells against rear wall 68 of the reaction chamber. The rotation speed is then reduced to approximately 2000 rpm and, with access ports 22, 24 and 26 sealed, air pressure is applied via central port 18 to drive fluid from the "C4" chamber into the "C5" chamber through channel 70. From the "C5" chamber, the fluid flows to retaining chambers "C6" and "C7" and excess air is vented from the "C8" chamber through air hole 36. The cells are then resuspended by adding resuspension fluid via tube 100 and port 18 to central channel 48 while centrifuging the disk at approximately 600 rpm to move the resuspension fluid from the central channel to the "C4" reaction chamber.

The packed cells are resuspended using the forward and reverse rotor action described above. The purpose of resuspending the red blood cells in this manner is to eliminate unbound antibody and to ensure that the subsequent pelleting and settling of the red blood cells occur in a medium of defined viscosity and density. When this operation is complete, the cells are again packed against rear wall 68 of the "C4" reaction chamber by centrifuging the disk at approximately 1000 rpm. Fluid remaining in the "C4" reaction chamber enhances the sensitivity of the agglutination process by buoying the cells, thereby minimizing the influence of differences in cell density upon cell aggregation and settling.

A single optical system located beneath optical windows 43, 46 in the "C4" reaction chamber monitors the packing of cells against rear wall 68 of the "C4" reaction chamber. The optical system is capable of taking optical readings while disk 9 is spinning. Any of a variety of standard techniques may be used to differentiate between cuvettes 14 within a single disk 9 as readings are being taken. These techniques include, but are not limited to, indexing the first cuvette or employing a coded indication on the first cuvette (or on a turntable on which disk 9 may rest) and counting to identify the location of radially sequential cuvettes. A coded indication may also be provided for each cuvette.

An important feature of the invention is its ability to photooptically detect very weakly aggregating reactants. The procedure for detecting and grading weakly agglutinated erythrocytes begins immediately after the red blood cells have been resuspended in the resuspension fluid. The amount of light passing through the suspension at this point and immediately thereafter, as the red blood cells are repelleted, is indicative of the aggregation strength of the red blood cells. When large aggregates are resuspended, they are broken up into only a few aggregates which block little of the light passing through the cuvette. Furthermore, the large aggregates are rapidly pelleted from suspension so the initial optical density of the cuvette rapidly decreases. Conversely, weak aggregates are broken up into many small aggregates which block most of the light passing through the cuvette and require much more time to pellet from suspension. Thus the hallmark of a weak aggregate is one which has a high optical density which slowly decreases.

Figure 7:
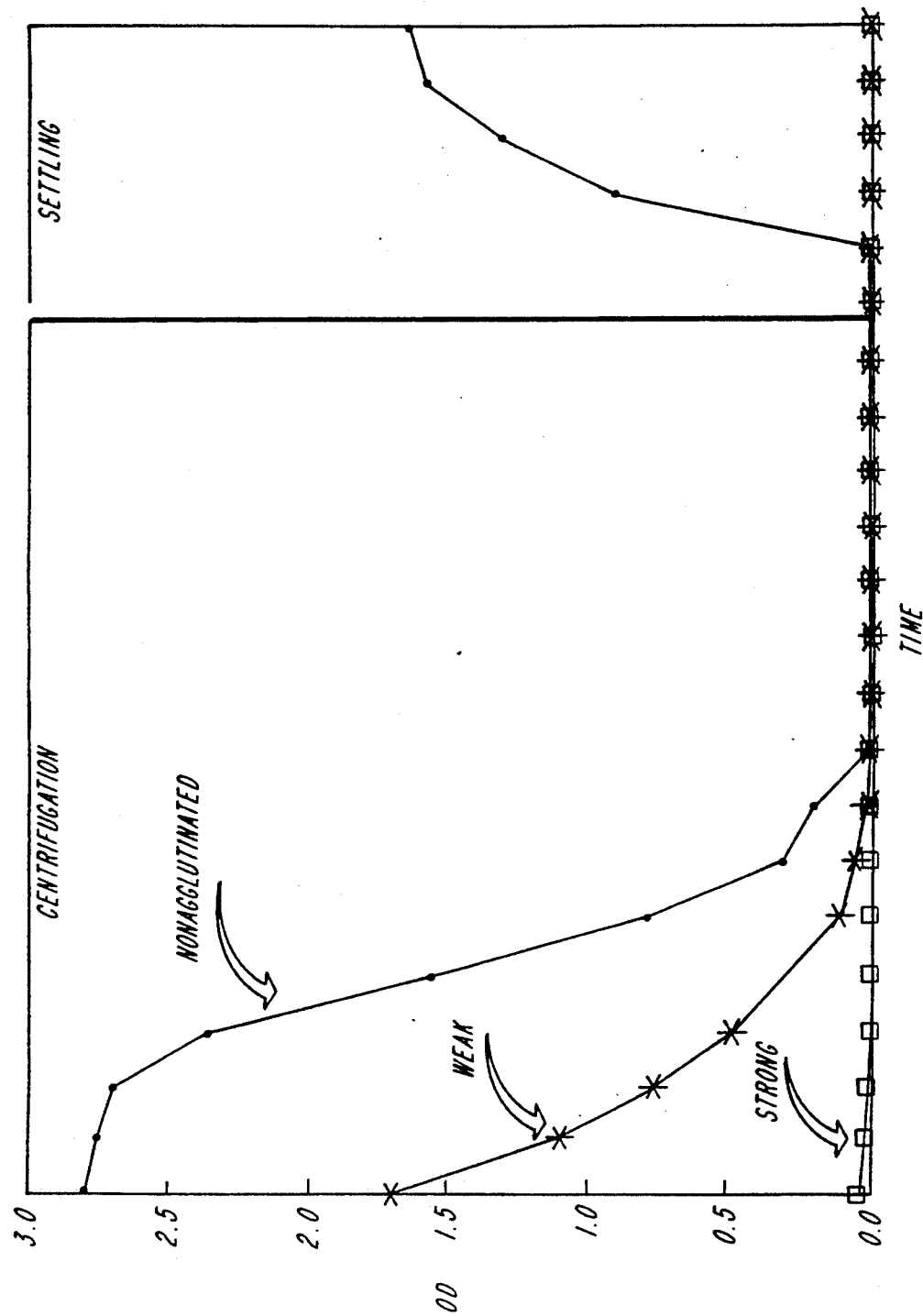
FIG. 7 is a plot of the optical density as a function of centrifugation and settling time.

The differences in the pelleting profiles of strong, intermediate and weak aggregates can be seen in FIG. 7. As shown in this figure, both pelletting and settling processes result in a change in the optical density of the cuvette as viewed through optical window 46. After pelleting is complete, disk rotation is slowed to 100 rpm where the optical density is again taken. The disk is then stopped for approximately 15 seconds and the optical density of each cuvette is determined again by rotating the disk at 100 rpm. The process of stopping the disk and taking the optical density of the cuvettes every 15 seconds is repeated another two times. The process of allowing the red blood cells to settle off of the rear wall when the disk has been stopped is employed because it is an especially sensitive measure of the strength of red blood cell aggregation. Red blood cells which are not aggregated settle rather rapidly. However, the rate of red blood cell settling diminishes to zero with even the slightest degree of aggregation. Red blood cells which have an aggregation strength above this limit do not settle.

The procedure for reverse blood typing is identical to that described for forward blood typing with the exception that patient plasma is placed in the "C3" chamber and reagent erythrocytes containing a known blood type in specific quantity ("reagent RBC") is placed in the "C1" chamber. The sera and cells are reacted and analyzed using the same procedure as specified above.

In addition to blood typing applications, the plasma or serum of a patient may be screened for the existence of particular antibodies by mixing the patient's plasma or serum with cells or particles that are known to carry the test antigen and determining whether agglutination results. Screening tests are slightly more complicated than blood typing tests because of the need for additional reaction steps. In a typical screening test, a sample of patient plasma is mixed with screening cells whose antigenic determinants are known. The procedure for reverse typing, described above, is then followed.

After the test used for reverse typing has been run to test for the presence of agglutination, the next phase of antibody screening is started. Disk 9 is then centrifuged at 4000 rpm to repack the cells against rear wall 68 of the "C4" reaction chamber. Saline and any remaining supernatant is driven off using the air purge pressure step described above.

Rotation is stopped and a second aliquot of patient plasma is introduced into the "C3" chamber via port 26. Disk 9 is centrifuged at approximately 500 rpm to drive patient plasma toward the screening cells located at the rear of the "C4" reaction chamber. Patient plasma and screening cells are mixed in the "C4" chamber using the forward and reverse rotor action described above. Disk 9 is then incubated for a specified time under conditions of controlled temperature and humidity to enhance the reaction between patient plasma and screening cells (e.g., to enhance a weak agglutination reaction). When incubation is complete, disk 9 is returned to the centrifuge and the cells are repacked by centrifugation at 4000 rpm. The fluid is driven from the "C4" reaction chamber and the pelleted cells are resuspended in saline according to the methods described above. The cells are then thoroughly washed using repetitive saline resuspension and air pressure/fluid removal steps as described earlier.

Following the final resuspension/wash cycle, disk 9 is brought to a standstill and Coombs anti-sera is added to the "C2" chamber via port 24. Coombs anti-sera is an antihuman globulin reagent and reacts with antibodies originating from the sample plasma that have become bound to test antigens located on the screening cells.

Disk 9 is centrifuged at 500 rpm to drive the Coombs anti-sera from the "C2" chamber into the "C4" reaction chamber. The Coombs anti-sera is then mixed with the screening cells previously packed against rear wall 68 of the reaction chamber using the forward and reverse rotor action described earlier. Disk 9 is centrifuged at approximately 1000 rpm to repack the cells against rear wall 68. The extent of aggregation is then determined by the process describe before for reverse typing. If antibody is present in patient plasma, the reaction of Coombs reagent and the bound antibodies will result in agglutination of the screening cells. Conversely, if sample plasma does not contain antibodies to the test antigen present on the surface of the screening cells, then Coombs anti sera will not agglutinate the screening cells.

For those cuvettes indicating a negative reaction, a cross check is undertaken to monitor the efficacy of the washing steps and demonstrate that the Coombs anti-sera was potent. In order to conduct the cross check, Coombs "check cells" are introduced into the "C1" chamber via port 22. Coombs "check cells" are IgG coated erythrocyte which will react positively (i.e., agglutinate) with the Coombs anti-sera. The "check cells" are driven into the "C4" reaction chamber by centrifuging disk 9 at 500 rpm. The "check cells" are mixed with the Coombs anti sera and screening cells using the forward and reverse rotor action described earlier. The cells are packed against rear wall 68 of the "C4" chamber by centrifuging disk 9 at 1000 rpm. The extent of aggregation is determined by the process previously described. If the Coombs "check cells" and the Coombs anti sera are operating correctly, a positive reaction (i.e., a slow increase in optical density as a function of settling time) will result. A negative reaction, indicating that the Coombs anti-sera is not potent, is indicated by rapid settling and hence a rapid increase in optical density during settling.

Although the embodiment described above has a multiplicity of chambers for containing, utilizing and disposing of fluid components of an agglutination reaction, it is possible to eliminate one or more of the chambers for alternative embodiments. Thus, reagents and samples may be sequentially introduced into the same chamber rather than separate chambers, and may be introduced directly into reaction chamber "C4" for some embodiments. Depending on the quantity of fluid to be removed from the reaction chamber and the method of removal, one or more of chambers "C5" and "C6" may also be eliminated. In the case where fluid is removed from the reaction chamber by vacuum (i.e., negative pressure only), a single chamber may be required into which fluids are added and within which the agglutination reaction is performed. This case is illustrated by a second embodiment of the invention shown in FIGS. 8-13.

Figure 8:
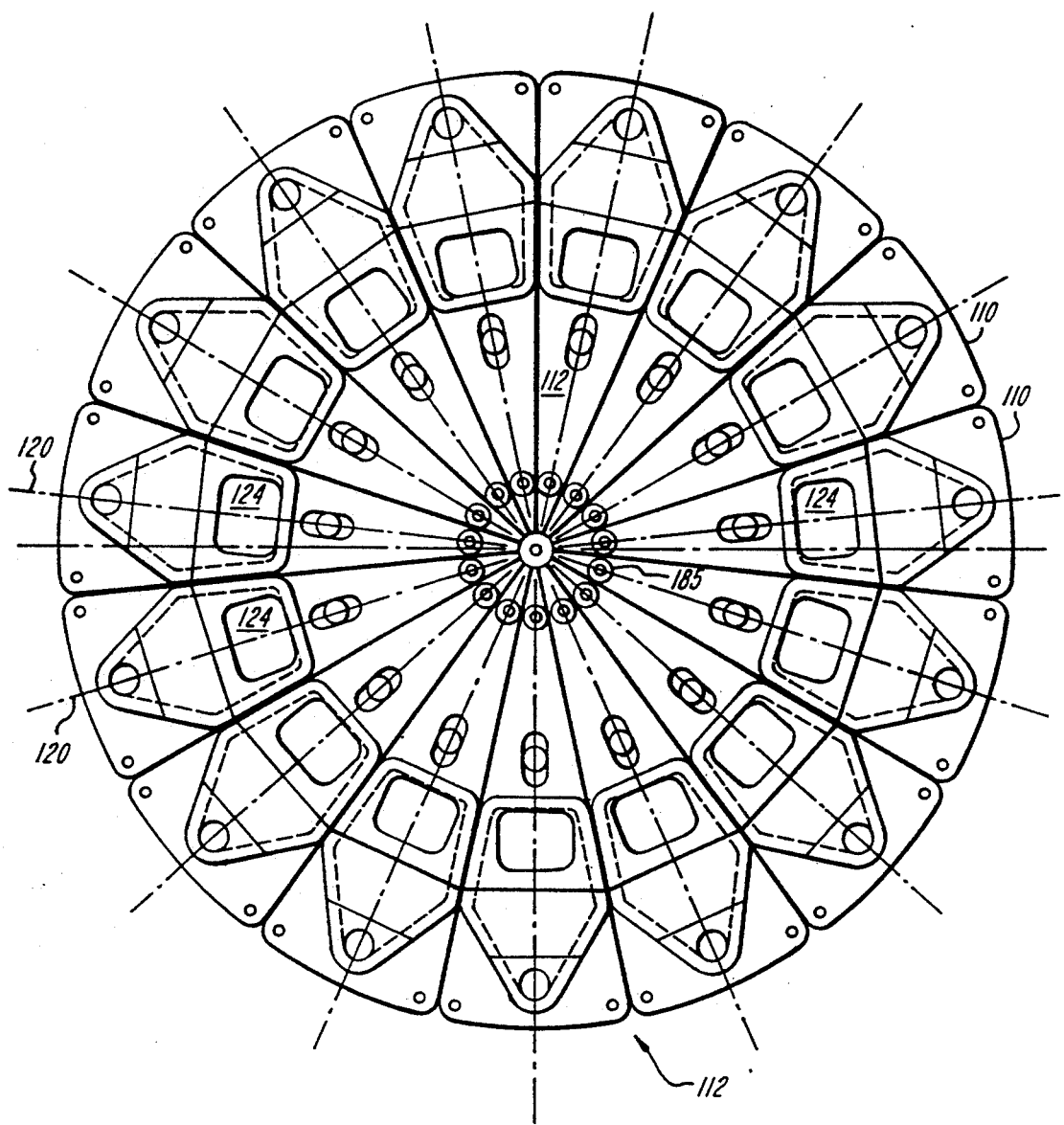
FIG. 8 is a top view of a plurality of cuvettes of a second embodiment of the invention arranged as a disk.

Referring to FIG. 8, a plurality of agglutination cuvettes 110 are shown arranged as a disk 112. The disk 112 contains fifteen identical cuvettes 110, each cuvette being generally wedge shaped from front to rear and symmetrical from side to side about a radius line 120 running centrally from front to rear. The radius line 120 defines the direction of force exerted on materials introduced into a cuvette when rotated about a centrifugal axis. For the purpose of illustration, the invention will be described with reference to a single agglutination cuvette 110; however, it should be understood that the invention generally includes a plurality of cuvettes either arranged as a unitary, multichambered disposable disk 112 or as separate cuvettes radially mounted as shown in FIG. 8.

Figure 9:
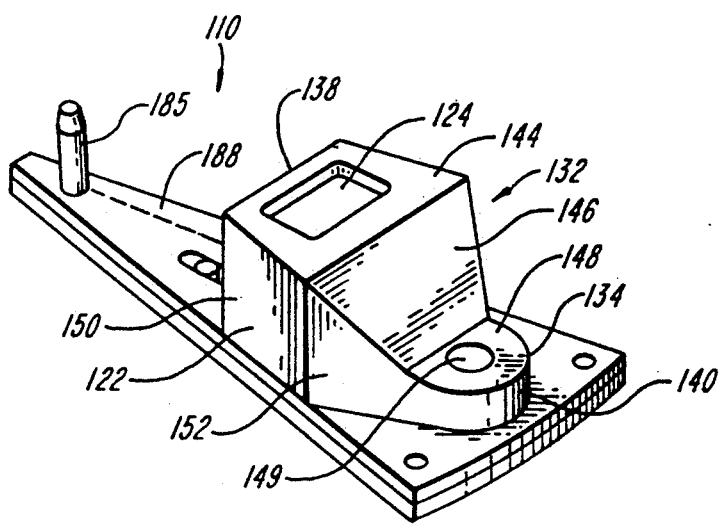
FIG. 9 is a side elevation perspective view of one of the cuvettes of FIG. 8.
Figure 10:
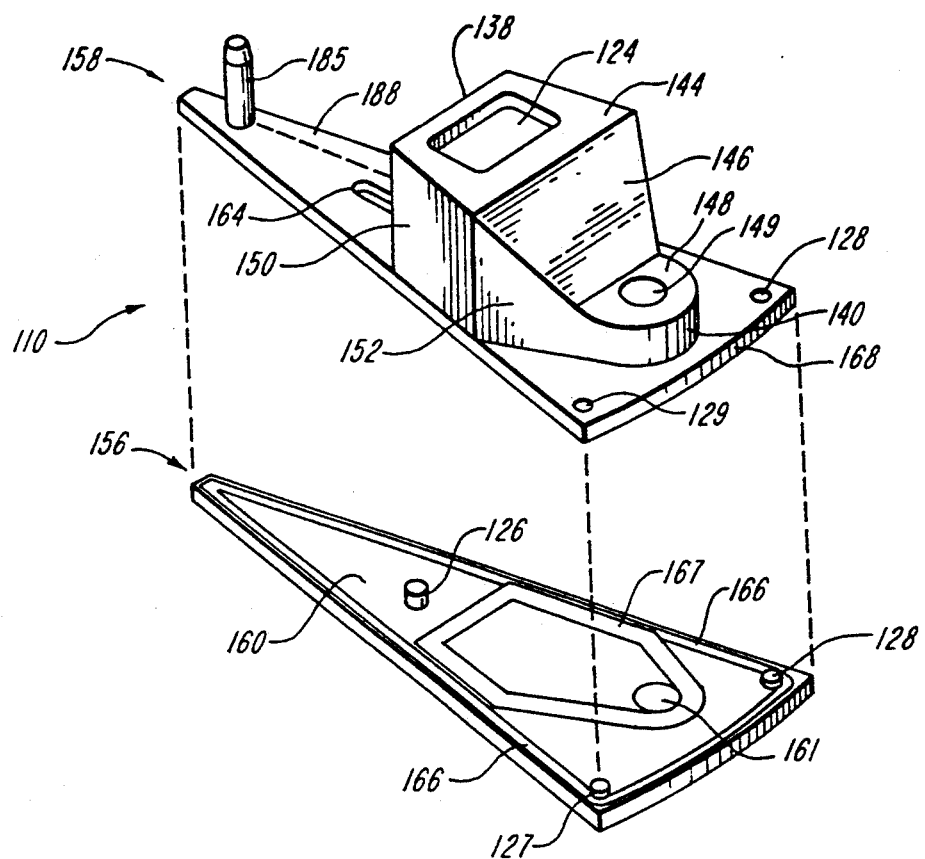
FIG. 10 is an exploded side elevation perspective view of the cuvette shown in FIG. 9 illustrating a two piece construction for this cuvette.

The overall configuration of each agglutination cuvette may be understood more particularly with reference to FIGS. 9 and 10. FIG. 9 is a side perspective view of a single cuvette of FIG. 8, while FIG. 10 is the same view exploded to illustrate the two-piece construction of the cuvette. The agglutination cuvette 110 is preferably formed of two injection molded pieces; bottom piece 156 and top piece 158. The top piece 158 has a substantially flat, generally wedge shaped top platform 168 with a pentagonal shaped chamber 122 formed thereon, rearward from its midsection. Chamber 122 is accessed through a port 124 formed in the top thereof. In an alternative embodiment, a larger opening in the top of chamber 122 is included in lieu of port 124. Thus, a stream of fluid directed at the opening during centrifugation of the cuvettes, is divided or split by the walls of the cuvettes, resulting in approximately the same amount of fluid entry into each chamber 122.

Generally, chamber 122 has heights and widths that define at least two and preferably three chamber portions. A radially inward front portion 130 has a uniform height and has a width that generally increases in cross section from front to rear; a radially intermediate portion 132 is generally funnel shaped with a height and width that progressively decreases in cross section from front to rear; and a radially outward rear portion 134, which will hereafter be referred to as the agglutination chamber, is generally rectangular in cross section terminating in a radially outward wall 140. Agglutination chamber 134 has a much smaller volume than the front and middle chamber portions 130 and 132. The combination of the progressively increasing cross section provided by radially inward portion 130 and the progressively decreasing cross section provided by radially intermediate portion 132 results in a chamber characterized by having a pelleting distance which does not change appreciably as a function of fluid volume. Because differences in fluid volume in the chamber do not appreciably change the pelleting distance of the particulate reactants, the shapes of the pelleting curves (FIG. 7) are stabilized, thereby facilitating interpretation of the pelleting curves and gradation of agglutination reaction strength.

Chamber 122 has a top wall in generally three sections which extends from the top of a front wall 138 to the top of radially outward wall 140. The top wall has a front top wall 144 extending parallel to top platform 168, and a mid top wall 146 downwardly sloping toward top platform 168. A rear top wall 148 extends parallel to top platform 168 and includes a first optical window 149 for optically communicating with agglutination chamber 134.

Chamber 122 includes side walls extending from the sides of the front wall 138 to the sides of radially outward wall 140. The side walls also have three sections mating with the three sections of the top wall and with top platform 168. Front side walls 150 are angled away from one other from front to rear and mate with front top wall 144 to form front chamber portion 130. Mid side walls 152 are angled toward one another from front to rear and meet at radially outward wall 140. Preferably, radially outward wall 140 is curvilinear; however, it can be of another shape, for example V-shaped. Thus, mid side walls 152 and mid top wall 146 together form the generally funnel shaped mid chamber portion 132 and mid side walls 152, rear top wall 148 and radially outward wall 140 together form agglutination chamber 134.

Figure 11:
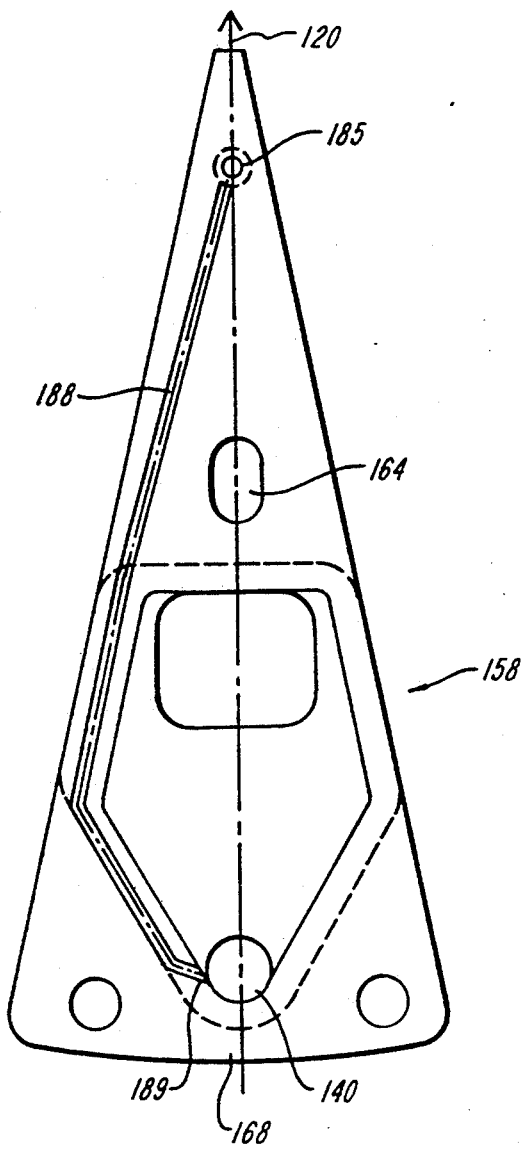
FIG. 11 is a bottom view of the top cuvette piece shown in FIG. 10.

Top platform 168 has an attachment slot 164 to align top piece 158 with bottom piece 156 and an exit pipe 185 to remove fluids or a fluid suspension from the cuvette. A channel 188 (FIG. 11) is cut into the bottom of top platform 168 and communicates at one end with exit pipe 185 and at an opposite end with a rear portion of cuvette chamber 122 Channel 188 has an entrance hole 189 located sufficiently close to radially outward wall 140 to effectively remove fluid from agglutination chamber 134, without removing reactants during centrifugation at a selected rate. Preferably, as shown in FIG. 11, channel 188 originates at exit pipe 185, extends parallel to an edge of top platform 168, along the length of top platform 168 and parallel to front side wall 150, along the length of front side wall 150. Channel 188 then angles inward toward radius line 120 and proceeds parallel to mid side wall 152, along the length of mid side wall 152. Subsequently, channel 188 angles toward radius line 120 and away from mid side wall 152 toward agglutination chamber 134. Channel 188 ends in entrance hole 189 at approximately the junction of mid side wall 152 and radially outward wall 140.

As shown in FIG. 10, bottom piece 156 of cuvette 110 is formed of a substantially flat, generally wedge-shaped bottom platform 160, sized to mate in facing relation with top platform 168 of top piece 158. Bottom platform 160 has one or more orientation pins 126 and 127 at its mid and rear sections. Orientation pin 126 mates with attachment slot 164 of top platform 168 and orientation pin 127 mates with attachment well 129 of top platform 16 to facilitate proper alignment. Both bottom platform 160 and top platform 168 include one or more holes 128 at their rear end as means to attach the cuvette to a device which will rotate the cuvette about a centrifugal axis (not shown). A second optical window 161 is located at the rear end of bottom platform 160 and aligned with first optical window 149 of chamber 134 to allow photodetection of reactants at radially outward wall 140.

Figure 12:
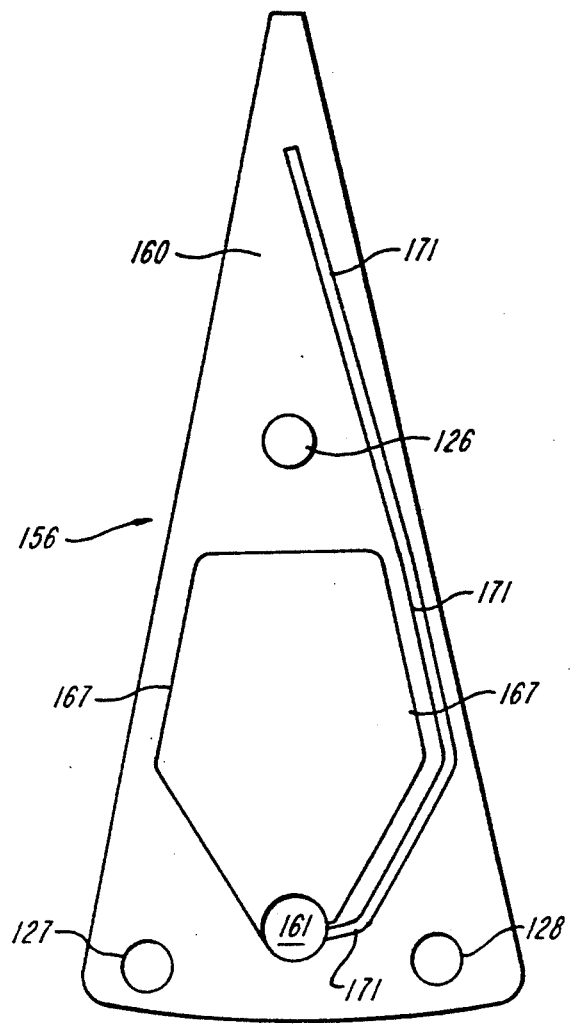
FIG. 12 is a top view of the bottom cuvette piece shown in FIG. 10.

As shown in FIG. 12, bottom platform 160 is provided with ridges for mating with top piece 158 and for forming cuvette chamber 122 and channel 188 with top piece 158. Bottom platform 160 has a pentagonal-shaped ridge 167 located near its mid section in alignment with the edges of the generally pentagonal-shaped cuvette chamber 122 of top piece 158. Bottom platform 160 also includes one or more inner ridges 171 which mate with the bottom of top platform 168, on both sides of channel 188.

When top piece 158 and bottom piece 156 are aligned, the pieces are pressed together and, for the preferred embodiment, ultrasonically welded. Ultrasonic welding results in the melting of ridges 167 and 171 on bottom platform 160, against the bottom of top platform 168 to secure the platforms to each other and to form a fluid tight channel 188 and chamber 122. Additionally, pins 126 and 127 of bottom platform 160 sealingly mate with slot 164 and well 129 of top platform 168, respectively.

Figure 13:
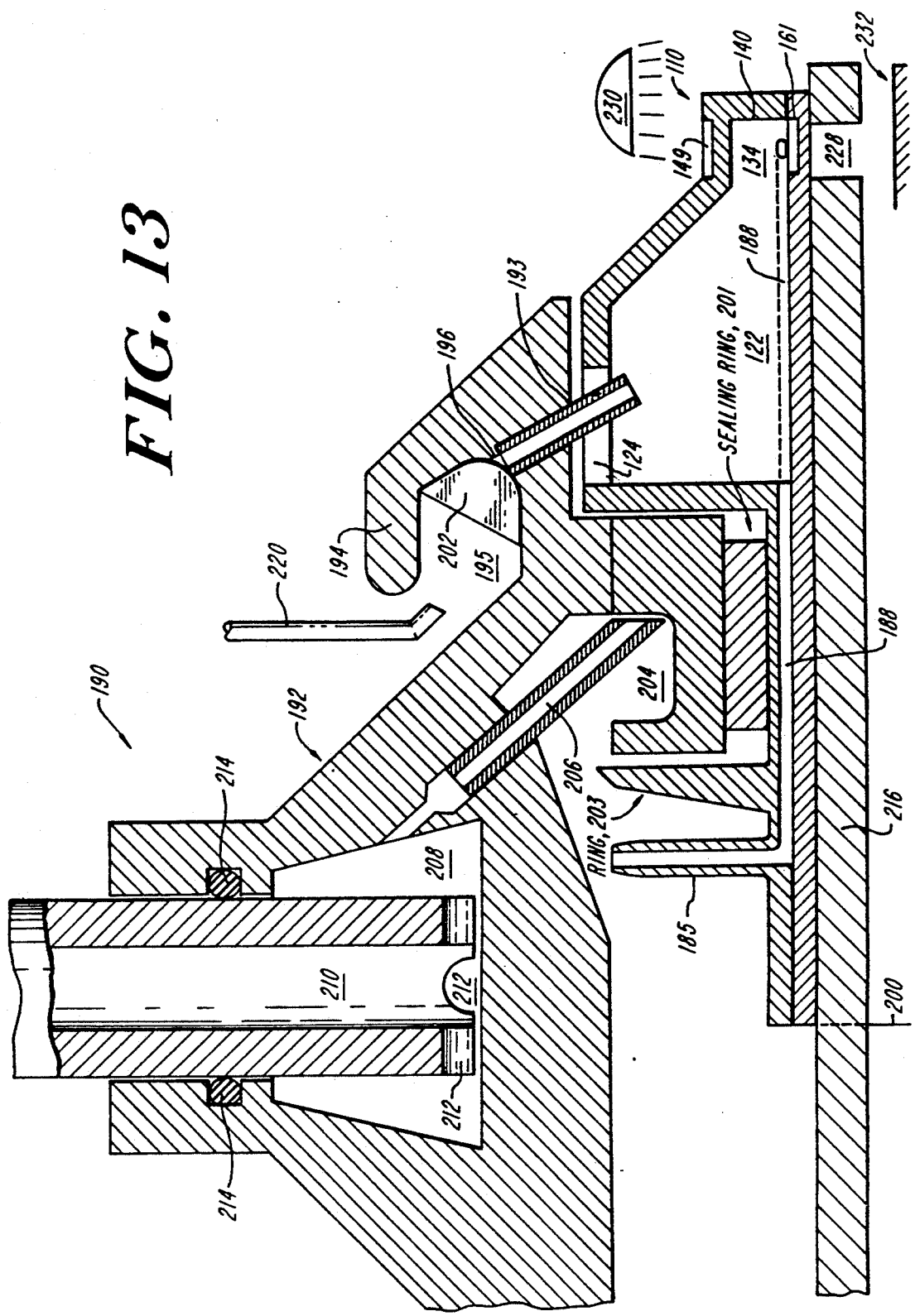
FIG. 13 is a side cross-sectional view of a hold down device and cuvette of FIG. 10 shown with the cuvette mounted on a representation of a centrifuge rotor and a photometric detection system for measuring the extent of agglutination.

The apparatus of the present invention can include a hold down device 190, as shown in FIG. 13 in communication with a cuvette 110 during centrifugation. Generally, hold down device 190 maintains cuvette 110 or a plurality of cuvettes arranged as a disk 112 in proper position during centrifugation, provides an airtight seal between cuvette 110 and hold down device 190 and withdraws or dispenses fluids or a fluid suspension to cuvette chamber 122 during centrifugation. Specifically, hold-down device 190 has a housing 192 which contains a series of fluid withdrawal pipes through which fluid or a fluid suspension is removed from cuvette chamber 122. A fluid dispensing tube 220 is included with hold down device 190 to dispense fluid to be added to cuvette 110, to resuspend particulate reactants in chamber 122.

Hold down device 190 is adapted for use with a conventional vacuum pump which provides the necessary vacuum pressure to withdraw fluids from cuvette chamber 122 (FIG. 13). Housing 192 includes a lip 194 and basin 195 to capture fluid dispensed by tube 220 to be added to cuvette chamber 122. An access port 196 and access tube 193 are provided for each cuvette 110 through which fluid captured in lip 194 and basin 195 is added to the corresponding cuvette chamber 122. Preferably, housing 192 has a divider 222, located in basin 195 on either side of each fluid access port 196 to capture a predetermined amount of fluid dispensed by fluid dispensing tube 220 to be introduced into cuvette chamber 122.

Hold down device 190 further includes a first fluid chamber 204. First fluid chamber 204 is generally rectangular in shape and provides a "catch-all" for fluid or fluid suspension withdrawn from cuvette chamber 122. Chamber 204 is in communication with a second fluid chamber 208 via a fluid withdrawal channel 206. Second fluid chamber 208 is generally in the shape of a truncated cone to force fluid withdrawn from fluid withdrawal channel 206 to the floor of second fluid chamber 208. A main air pipe 210 communicates with second fluid chamber 208 when the hold down device is attached to a vacuum pump. When properly positioned, main air pipe 210 is perpendicular to the floor of second fluid chamber 208 and includes four half moon shaped cut outs 212 to allow fluids or a fluid suspension to be completely withdrawn from second fluid chamber 208. A set of o-rings 214 are included in hold down device 190 to sealingly mate and maintain main air pipe 210 in proper position.

Hold-down device 190 is adapted to withdraw or dispense fluid when a cuvette 110, or plurality of cuvettes arranged as a disk 112, is rotated on a centrifuge rotor. Specifically, hold down device 190 can withdraw or dispense fluid to cuvette 110 through a tube 220 during centrifugation and, thus, allows for repeated washing of reactants in a single reaction vessel (e.g., cuvette 110). Additionally, the series of fluid withdrawal channels of hold-down device 190 is designed such that fluid once withdrawn from the cuvette chamber 122 cannot return to the cuvette 110, even if centrifugation is discontinued.

When a plurality of cuvettes are arranged as in disk 112 (figure 8) and positioned on a centrifuge rotor, it is possible to use a design which incorporates a tapered ring 203 built into the unitary structure which is radially outward of pipe 185 (FIG. 13). A sealing ring 201 or gasket in hold down 190 contacts the disk so that a vacuum can be drawn and ensures that fluid enters and is collected in first fluid chamber 204. In operation, the cuvettes are rotating when a vacuum is drawn, pulling fluid out of the cuvettes via pipe 185. Fluid is transferred to chamber 204 via differential pressure and centrifugal force. Once in chamber 204 the fluid is transferred through 206, 208, 212 and 210.

As described above with reference to the first embodiment, the apparatus of the present invention can be used to type and screen blood. When proceeding with cuvette 110 or a plurality of cuvettes arranged as a disk 112 (see FIG. 8) the proper cells, plasma and antiserum are loaded into cuvette 110 through port 124. Cuvette 110 is placed onto a centrifuge rotor 216 and under a hold down device 190 as shown in FIG. 13. The centrifuge rotor includes a hole 228, which is aligned with optical windows 149 and 161 of each cuvette to allow photodetection of reactants in the cuvette chamber. The reactants are mixed together briefly (1–2 seconds) by oscillating the cuvette at approximately 500 rpm. A short incubation period of 5–10 seconds is then allowed, followed by centrifugation at approximately 4000 rpm. When the rotor is spun, the contents of cuvette 110 are hurled radially outwardly by centrifugal force into agglutination chamber 134. Cuvette 110 may be sized such that, for example, a 40 microliter test sample will fill agglutination chamber 134. Particulate reactants in the sample will separate from fluid during centrifugation, moving toward radially outward wall 140 of each cuvette 110

After centrifugation, fluid is withdrawn from agglutination chamber 134, through channel 188 and into hold-down device 190 by vacuum pressure at exit pipe 185 as described above with reference to FIG. 13. Fluid can be withdrawn while centrifuging or when the device is stationary. Preferably, the device is rotated at approximately 2000 rpm while the fluid is withdrawn to ensure that cells will remain packed against the radially outward wall 140. Subsequently, the reactants are resuspended by the addition of saline from the fluid dispensing tube 220. The device is briefly oscillated again to resuspend the erythrocytes.

After resuspension, the erythrocytes are pelleted against the back wall by centrifugation at 1000 rpm. The relative strength of agglutination (including weakly agglutinating reactants) can be determined by examining the amount of light which passes through first and second optical windows 149 and 161 of cuvette 110 as the reactants are pelleted against the radially outward wall 140 of the agglutination chamber 134. Optical density (OD) readings are taken using a conventional photometric detection system which includes a light source 230 and a light beam detector 232 (FIG. 13). For example, erythrocytes which aggregate strongly, form aggregates while they are pelleting. These aggregates do not block as much light as do unaggregated or weakly aggregated erythrocytes. The difference in the patterns of light blockage by aggregates of different strength are shown in FIG. 7.

Preferably, cuvette 110 is centrifuged at approximately 1000 rpm and OD readings are taken continuously while the centrifuge is brought up to speed. After the reactants have been pelleted against the radially outward wall 140, centrifugation is ceased. At this point, non agglutinated and agglutinated reactants can be differentiated, as non-agglutinated reactants settle under the influence of gravity (see "settling" FIG. 7). If the reactants are not aggregated, they will slide off radially outward wall 140 and occlude light passing through cuvette 110. In order to photodetect a plurality of cuvettes arranged as a disk 112, the disk is rotated at approximately 100 rpm to repeatedly photodetect each cuvette 110 as reactants settle.

The operation of the device has been described in connection with determining blood type and screening assays. However, it should be understood that this description of the operation of the device applies to other immunologic reactions. Reactants useful in the present invention include, but are not limited to reagents, biological specimens or samples used in protein, immunological and affinity assays. Reactants can include antibodies and antigens, including antibodies and antigens attached to substrates (e.g., cells, latex particles). In general, reactants are introduced into the cuvette chamber suspended in a fluid such as serum, plasma, saline or albumin and additional reactants can be added to the fluid suspension.

It should be understood that various changes and modifications to the foregoing embodiments may be made within the scope of this invention. For example, when a plurality of cuvettes are arranged as a disk, the entire disk can be manufactured as two pieces, rather than as individual cuvettes assembled onto a rotor. In this manner, the cuvettes are integral with the disk.

Thus, it is intended that all matter contained in the above description or shown in the accompanying drawings is to be interpreted as illustrative and that the foregoing and other changes is form and detail may be made therein while still remaining within the spirit and scope of the invention.

What is claimed is:

1. An apparatus for analyzing reactants contained in a fluid and adapted for use with a device which will rotate the apparatus about a centrifugal axis comprising, at least one cuvette, said cuvette having at least one chamber, said chamber having a radially outward wall which provides a base upon which the reactants are pelleted when the apparatus is rotated about a centrifugal axis, means for introducing fluids into said chamber, and a channel for removing fluid from said chamber, said channel having an entrance hole positioned and arranged adjacent and radially inward relative to said radially outward wall, and means for applying differential pressure to said chamber to force said fluids from said chamber through said channel during centrifugation.

2. An apparatus as claimed in claim 1, further comprising an exit pipe located radially inward of said chamber, and wherein said channel communicates at one end with said chamber and at an opposite end with said exit pipe.

3. An apparatus as claimed in claim 2, wherein said chamber has first and second portions, said first portion being located radially inward of said second portion, wherein said first portion has a top portion and herein said means for introducing fluids is a port located in said top portion of said first portion and wherein said radially outward wall is located in said second portion.

4. An apparatus as claimed in claim 3, further comprising optical window means formed in said chamber for photooptical detection of an agglutination reaction.

5. An apparatus as claimed in claim 2, wherein said exit pipe has a small diameter such that surface tension will stop capillary flow at an exit of said exit pipe.

6. An apparatus for analyzing reactants contained in a fluid and adapted for use with a device which will rotate the apparatus about a centrifugal axis comprising, at least one cuvette, including first, second and third chambers, said third chamber being located radially outward of said firs and second chambers, wherein said chambers are in selective fluid communication, and include means for preventing fluid flow between said chambers in the absence of a predetermined minimum centrifugal force, said third chamber including optical window means formed therein for photoanalysis of said reactants, said third chamber further including a radially outward wall which provides a base upon which the reactants are pelleted when the apparatus is rotated about a centrifugal axis, means for introducing fluids into said third chamber and a channel for removing fluid from said third chamber, said channel having an entrance hole positioned and arranged adjacent and radially inward relative to said radially outward wall, and means for applying differential pressure to said third chamber to force said fluids form said third chamber through said channel during centrifugation.

7. An apparatus as claimed in claim 6, wherein said third chamber includes a side wall with an obtuse angle bend.

8. An apparatus as claimed in claim 7, further comprising a fourth chamber in fluid communication with said third chamber, and wherein said fourth chamber is located radially inward from said third chamber, said fourth chamber including an access port and means for preventing fluid flow between said fourth chamber and said third chamber in the absence of a predetermined minimum centrifugal force.

9. An apparatus as claimed in claim 8, further comprising a fifth chamber in fluid communication with said channel and in fluid communication with at least one retaining chamber located radially outward from said fifth chamber, said retaining chamber collecting fluids forced from said third chamber.

10. An apparatus as claimed in claim 9, including a venting chamber located radially inward from said retaining chamber, means for permitting air flow from said retaining chamber to said venting chamber, and an air hole near a radially inward end of said venting chamber through which air may be vented.

11. An apparatus as claimed in claim 6, wherein said means for introducing fluids includes at least one of a central channel or a port formed in said cuvette.

12. An apparatus as claimed in claim 11, wherein there are a plurality of said cuvettes, and including a hold-down device for maintaining said plurality of cuvettes in proper position during centrifugation, said hold-down device having, means for sealing at least one port of each of said plurality of cuvettes, a housing, a pipe passing through said housing through which gas is introduced to or withdrawn from said plurality of cuvettes during centrifugation, and a fluid dispensing tube through which fluid is introduced to said plurality of cuvettes during centrifugation.

13. An apparatus as claimed in claim 12, wherein said housing further includes a basin to capture fluid dispensed by said fluid dispensing tube, a lip integral with said basin to facilitate fluid aperture, an access port formed in said basin through which fluid exits said basin, and an access tube through which fluid flows from said basin through said access port to said chambers of said plurality of said cuvettes.

14. An apparatus as claimed in claim 13, wherein said means for sealing is a gasket.

15. An apparatus as claimed in claim 14, wherein each of said plurality of said cuvettes includes at least one port having an internal taper and a protruding upper edge, thereby effectively increasing the pressure of said hold-down on said gasket by providing a discrete surface area upon which said gasket may be placed.

16. A hold-down device for maintaining a plurality of cuvettes in proper position during centrifugation and for adding or withdrawing fluids from said cuvettes during centrifugation comprising, a housing including, a pipe through said housing through which gas is introduced to or withdrawn from said plurality of cuvettes during centrifugation, a fluid dispensing tube through said housing, a basin for delivering said fluid to said plurality of cuvettes during centrifugation, said basin positioned and arranged in relation to said fluid dispensing tube so as to capture fluid dispensed by said fluid dispensing tube, and means for forming a seal between said hold-down device and said cuvettes.

17. A hold-down device for maintaining a plurality of cuvettes in proper position during centrifugation and for adding a or withdrawing fluids from said cuvettes during centrifugation comprising, a housing including, a pipe through said housing through which gas is introduced to or withdrawn from said plurality of cuvettes during centrifugation, a fluid dispensing tube through said housing though which fluid is introduced to said plurality of cuvettes during centrifugation, a basin to capture fluid dispensed by said fluid dispensing tube, a lip integral with said basin to facilitate fluid capture, an access port in said basin through which fluid exits said basin, and an access tube through which fluid flows from said basin through said access port to said plurality of said cuvettes; and means for forming a seal between said hold-down device and said plurality of said cuvettes.

18. A hold-down device as claimed in claim 17, further comprising dividers formed in said basin between said access ports to collect a controlled amount of fluid for delivery to said chambers of said plurality of said cuvettes.

19. An agglutination cuvette for analyzing reactants contained in a fluid, the cuvette adapted for use with a device which will rotate the cuvette about a centrifugal axis, said cuvette comprising;

at least one chamber with a radially outward wall providing a base upon which the agglutinated reactants are pelleted during centrifugation, means for introducing fluids into said cuvette, and at least one channel for removing said fluids from said chamber during centrifugation, said channel having an entrance hole positioned and arranged adjacent to and radially inward relative to said radially outward wall.

20. An agglutination cuvette as claimed in claim 19, further comprising an exit pipe located radially inward of said chamber, and wherein said channel communicates at one end with said chamber and at an opposite end with said exit pipe.

21. An agglutination cuvette as claimed din claim 20, wherein said chamber has first and second portions, said first portion being located radially inward of said second portion, wherein said means for introducing fluids is a port located in said first portion and wherein said radially outward wall is located in said second portion.

22. An agglutination cuvette as claimed in claim 21, further comprising optical window means formed in said chamber for photooptical detection of said agglutination reaction.

23. An agglutination cuvette as claimed in claim 20, wherein said exit pipe has a small diameter such that surface tension will stop capillary flow at an exit of said exit pipe.

24. An agglutination cuvette for analyzing reactants, the cuvette adapted for use with a device which will rotate the cuvette about a centrifugal axis, said cuvette comprising;
first, second and third chambers, said third chamber being located radially outward of said first and second chambers, wherein said chambers are in selective fluid communication, and including means for preventing fluid flow between said chambers in the absence of a predetermined minimum centrifugal force, said third chamber including a radially outward wall providing a base upon which the agglutinated reactants are pelleted during centrifugation, means for introducing fluids into said cuvette, and at least one channel positioned adjacent to said radially outward wall for removing said fluids from said chamber during centrifugation, said channel having an entrance hole positioned and arranged adjacent and radially inward relative to said radially outward wall, said third chamber further including optical window means formed therein for photooptical analysis of the reactants.

25. An agglutination cuvette as claimed in claim 24, wherein said third chamber includes a side wall with an obtuse angle bend.

26. An agglutination cuvette as claimed in claim 25, further comprising a fourth chamber in fluid communication with said third chamber, and wherein said fourth chamber is located radially inward from said third chamber, said fourth chamber including an access port and means for preventing fluid flow between said fourth chamber and said third chamber in the absence of a predetermined minimum centrifugal force.

27. An agglutination cuvette as claimed in claim 26, further comprising a fifth chamber in fluid communication with said channel and in fluid communication with at least one retaining chamber located radially outward from said fifth chamber, said retaining chamber collecting fluids forced from said third chamber.

28. An agglutination cuvette as claimed in claim 27, including a venting chamber located radially inward from said retaining chamber, means for permitting air flow from said retaining chamber to said venting chamber, and an air hole near a radially inward end of said venting chamber through which air may be vented.

29. An agglutination cuvette as claimed in claim 24, wherein said means for introducing fluids includes at least one of a central channel or a port formed in said cuvette.

30. An apparatus for analyzing reactants contained in a fluid and adapted for use with a device which will rotate the apparatus about a centrifugal axis comprising,
at least one cuvette, said cuvette having at least one cuvette chamber, said cuvette chamber having a radially outward wall which provides a base upon which reactants are pelleted when the apparatus is rotated about a centrifugal axis, means for introducing fluids into said cuvette chamber, and a channel positioned adjacent to said wall for removing fluid from said cuvette chamber;
means for applying differential pressure to said cuvette chamber to force said fluids from said cuvette chamber through said channel during centrifugation; and
at least one fluid chamber for receiving said fluids forced by differential pressure from said cuvette chamber.

31. An apparatus as claimed in claim 30, further comprising an exit pipe located radially inward of said cuvette chamber, and wherein said channel communicates at one end with said cuvette chamber and at an opposite end with said exit pipe.

32. An apparatus as claimed in claim 31, wherein said exit pipe has a small diameter such that surface tension will stop capillary flow at an exit of said exit pipe.

33. An apparatus as claimed in claim 31, wherein said cuvette chamber has first and second portions, said first portion being located radially inward of said second portion, wherein said first portion has a top portion, and wherein said means for introducing fluids is a port located in said top portion of said first portion and wherein said radially outward wall is located in said second portion.

34. An apparatus as claimed in claim 33, further comprising optical window means formed in said cuvette chamber for photooptical detection of said agglutination reaction.

* * * * *